United States Patent [19]

Copp et al.

[11] Patent Number: 4,564,684
[45] Date of Patent: Jan. 14, 1986

[54] 3-AMINO-1-PHENYL-2-PYRAZOLINES

[76] Inventors: Frederick C. Copp, Rotherwood, 32 Stanley Ave., Beckenham, Kent; Albert G. Caldwell, 119 Gates Green Rd., West Wickham, Kent; David Collard, 25 The Mead, Beckenham, Kent, all of England

[21] Appl. No.: 614,371

[22] Filed: May 23, 1984

Related U.S. Application Data

[63] Continuation of Ser. No. 256,072, Apr. 21, 1981, abandoned.

[30] Foreign Application Priority Data

Dec. 16, 1980 [GB] United Kingdom ............... 8040172

[51] Int. Cl.$^4$ .................. A61K 31/415; C07D 231/06
[52] U.S. Cl. .................................... 548/362; 548/379
[58] Field of Search ............................... 548/362, 379

[56] References Cited

U.S. PATENT DOCUMENTS 2,726,248 12/1955 Kendall et al. ..................... 548/362
4,149,005 4/1979 Battisti et al. ....................... 548/362

FOREIGN PATENT DOCUMENTS 682865 8/1979 U.S.S.R. .

OTHER PUBLICATIONS

Elguero et al. I, Bull. Soc. Chim. France 1970, No. 4, pp. 1576–1581.
Elguero et al. II, Bull. Soc. Chim. France 1969, No. 5, pp. 1683–1686.
Higgs et al., Chem. Abst. 1980, vol. 92, No. 15404h.
Duffin et al., J. Chem. Soc. 1954, pp. 408–415.

Primary Examiner—Richard A. Schwartz
Assistant Examiner—Kurt G. Briscoe
Attorney, Agent, or Firm—Donald Brown

[57] ABSTRACT

Heterocyclic compounds of formula (I) and acid addition salts thereof inhibit arachidonic acid oxygenation and are useful in medicine, for example as anti-inflammatory agents.

$$Ar-N\underset{R^4}{\overset{N}{\diagdown}}\underset{R^5}{\diagup}C-N\overset{R}{\underset{R^1}{\diagdown}} \quad (I)$$

The compounds of formula (I) may be prepared by any method analogous to those known in the art, for example by the method of G. F. Duffin and J. D. Kendall in J. Chem. Soc. (1954), 408–415. When used in medicine, the compounds of formula (I) may be administered as the compound alone or as a pharmaceutical formulation together with a pharmaceutically acceptable carrier.

5 Claims, No Drawings

3-AMINO-1-PHENYL-2-PYRAZOLINES

This application is a continuation, of application Ser. No. 256,072, filed 04/21/81 now abandoned.

This invention relates to formulations comprising heterocyclic compounds and their preparation, to their use in medicine in a mammal, including man, e.g. as anti-inflammatory or anti-allergic agents or as agents in the prevention of tissue rejection, and to certain novel heterocyclic compounds and their preparation.

In their studies on the reaction of diazonium salts with 1-aryl-2-pyrazolines, Duffin and Kendall (J. Chem. Soc., (1954), 408–415) produced 3-ethylamino-1-phenyl-2-pyrazoline (page 409 and 413) in tests to identify the product of an earlier reaction. It has now been found that related compounds of formula (I) inhibit both the lipoxygenase and cyclooxygenase pathways of arachidonic acid metabolism in vitro and are useful as anti-inflammatory or anti-allergic agents or as agents in the prevention of tissue rejection and other medical conditions alleviated by the inhibition of arachidonic acid oxygenation.

Accordingly, the present invention relates to heterocyclic compounds of formula (I) and acid addition salts thereof:

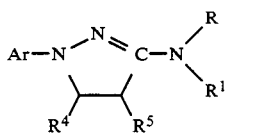
(I)

wherein,
Ar is selected from monocyclic and bicyclic aromatic radicals having from 5 to 10 ring atoms selected from carbon and nitrogen, which aromatic radical is optionally substituted in any position of the ring by one or more substituent(s);
R is selected from hydrogen, alkyl (optionally substituted by a substituent selected from phenyl or cycloalkyl of from 3 to 6 carbon atoms), alkenyl and alkynyl; $R^1$ is selected from alkyl (optionally substituted by a substituent selected from phenyl or cycloalkyl of from 3 to 6 carbon atoms), alkenyl and alkynyl; and $R^4$ and $R^5$ are the same or different and are each selected from hydrogen and alkyl.

In this specification, 'alkyl', 'alkenyl', and 'alkynyl' groups each have from 1 to 6 carbon atoms.

Examples of aromatic radicals include phenyl, naphthyl, quinolyl and pyridyl. Particularly preferred aromatic radicals are phenyl and pyridyl, especially wherein 'pyridyl' is selected from 2-pyridyl and 4-pyridyl. The aromatic ring is preferably substituted and examples of suitable substituents are halo, alkyl (which may itself be optionally substituted by halo), carboxy, alkoxy, amino (which may itself be optionally substituted by 1 or 2 alkyl groups), hydroxy and alkylsulphonyl of which the alkyl moiety may itself be optionally substituted by halo. Examples of especially suitable Ar substituents are halo (that is: fluoro, chloro, bromo and iodo), tert-butyl and trifluoromethyl. When Ar is phenyl, the preferred positions of the ring for any substituent are those selected from the 2-, 3-, 4-, 3,4- and 2,6-positions. For example, Ar may be selected from 3-trifluoromethylphenyl, 4-trifluoromethylphenyl, 4-fluorophenyl, 4-chlorophenyl, 4-bromophenyl, 3-trifluoromethyl-4-fluorophenyl, 3-trifluoromethyl-4-chlorophenyl and 3-trifluoromethyl-4-bromophenyl. When Ar is pyridyl, the preferred positions of the ring for any substituent are those selected from the 5- and 6-positions. For example, Ar may be selected from 5-chloro-2-pyridyl, 5-bromo-2-pyridyl and 5-iodo-2-pyridyl.

$R^4$ and $R^5$ are preferably selected from hydrogen and methyl. $R^1$ is preferably selected from alkyl and benzyl. R is preferably selected from hydrogen, alkyl and benzyl and more preferably from hydrogen and alkyl. For example, compounds of formula (I) when R is hydrogen and $R^1$ is alkyl such as methyl are especially preferred.

Examples of compounds of formula (I) are:
3-(methylamino)-1-(3-trifluoromethylphenyl)-2-pyrazoline;
3-(ethylamino)-1-(3-trifluoromethylphenyl)-2-pyrazoline;
3-(n-propylamino)-1-(3-trifluoromethylphenyl)-2-pyrazoline;
3-(iso-propylamino)-1-(3-trifluoromethylphenyl)-2-pyrazoline;
3-(n-butylamino)-1-(3-trifluoromethylphenyl)-2-pyrazoline;
3-(sec-butylamino)-1-(3-trifluoromethylphenyl)-2-pyrazoline;
3-(tert-butylamino)-1-(3-trifluoromethylphenyl)-2-pyrazoline;
3-(benzylamino)-1-(3-trifluoromethylphenyl)-2-pyrazoline;
3-(N,N-dimethylamino)-1-(4-trifluoromethylphenyl)-2-pyrazoline;
3-(N-methyl-N-ethylamino)-1-(4-chlorophenyl)-2-pyrazoline;
3-(methylamino)-1-(4-fluorophenyl)-5-methyl-2-pyrazoline;
3-(benzylamino)-1-(4-bromophenyl)-4-methyl-2-pyrazoline;
3-(ethylamino)-1-(3-trifluoromethyl-4-fluorophenyl)-2-pyrazoline;
3-(tert-butylamino)-1-(3-trifluoromethyl-4-bromophenyl)-2-pyrazoline;
3-(iso-propylamino)-1-(5-chloro-2-pyridyl)-2-pyrazoline;
3-(methylamino)-1-(5-bromo-2-pyridyl)-2-pyrazoline;
3-(benzylamino)-1-(5-iodo-2-pyridyl)-2-pyrazoline;
3-(allylamino)-1-(3-trifluoromethylphenyl)-2-pyrazoline;
3-(cyclohexylmethylamino)-1-(3-trifluoromethylphenyl)-2-pyrazoline.

A novel subclass of the compounds of formula (I) is the compounds of formula (IA):

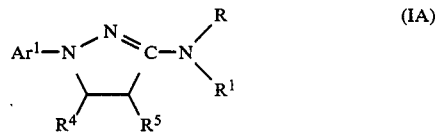
(IA)

wherein,
$Ar^1$ is selected from monocyclic aromatic radicals (other than phenyl) and bicyclic aromatic radicals having from 5 to 10 ring atoms selected from carbon and nitrogen, which aromatic radical is optionally substituted in any position of the ring by one or more substituent(s);
R is selected from hydrogen, alkyl (optionally substituted by a substituent selected from phenyl and cycloalkyl of from 3 to 6 carbon atoms), alkenyl and alkynyl;

R¹ is selected from alkyl (optionally substituted by a substituent selected from phenyl and cycloalkyl of from 3 to 6 carbon atoms), alkenyl and alkynyl; and R⁴ and R⁵ are the same or different and are each selected from hydrogen and alkyl;

and acid addition salts thereof.

A further novel subclass of the compounds of formula (I) is the compounds of formula (IB):

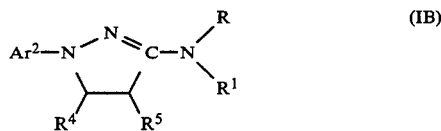

wherein,

Ar² is a monocyclic aromatic radical selected from phenyl substituted in any position of the ring by one or more substituent(s);

R is selected from hydrogen, alkyl (optionally substituted by a substituent selected from phenyl and cycloalkyl of from 3 to 6 carbon atoms), alkenyl and alkynyl;

R¹ is selected from alkyl (optionally substituted by a substituent selected from phenyl and cycloalkyl of from 3 to 6 carbon atoms), alkenyl and alkynyl; and R⁴ and R⁵ are the same or different and are each selected from hydrogen and alkyl;

and acid addition salts thereof.

A still further novel subclass of the compounds of formula (I) is the compounds of formula (IC):

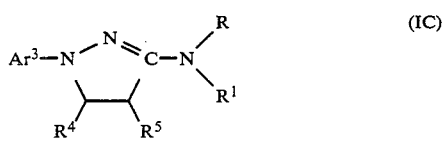

wherein,

Ar³ is an unsubstituted phenyl group;

R is selected from alkyl (substituted by a substituent selected from phenyl and cycloalkyl of from 3 to 6 carbon atoms), alkenyl and alkynyl;

R¹ is selected from alkyl (substituted by a substituent selected from phenyl and cycloalkyl of from 3 to 6 carbon atoms), alkenyl and alkynyl; and R⁴ and R⁵ are the same or different and are each selected from hydrogen and alkyl; and acid addition salts thereof.

However, a preferred subclass of the compounds of formula (I), within the subclasses of formulae (IA) and (IB) described above, is the compounds of formula (ID):

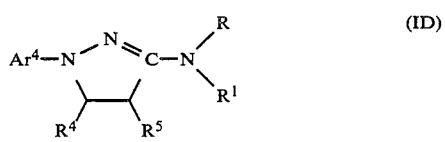

wherein,

Ar⁴ is a monocyclic aromatic radical selected from pyridyl which is optionally substituted in any position of the ring by one or more substituent(s); and phenyl substituted in any position of the ring by one or more substituent(s);

R is selected from hydrogen and alkyl (optionally substituted by phenyl);

R¹ is alkyl (optionally substituted by phenyl); and

R⁴ and R⁵ are the same or different and are each selected from hydrogen and alkyl; and acid addition salts thereof.

When used in medicine, the acid addition salts of a compound of formula (I) should be both pharmacologically and pharmaceutically acceptable acid addition salts, but non-acceptable salts may conveniently be used to prepare the bases of such acceptable salts and are not excluded from the scope of this invention. Acceptable salts may be derived from organic acids, particularly dicarboxylic acids. Such pharmacologically and pharmaceutically acceptable salts include those prepared from the following acids: hydrochloric, hydrobromic, sulphuric, nitric, phosphoric, oxalic, fumaric, maleic, glycolic, salicylic, succinic, toluene-p-sulphonic, tartaric, acetic, citric, methane sulphonic, formic, benzoic, malonic, naphthalene-2-sulphonic and benzene sulphonic.

The compounds of formula (I) may be prepared by any method analogous to those known in the art, for example by the method of G F Duffin and J D Kendall in J. Chem. Soc. (1954), 408–415.

(1) A method for preparing a compound of formula (I) comprises cyclisation and elimination of water from a compound of formula (II) and optionally converting it to any other desired compound of formula (I).

wherein R, R¹, R⁴, R⁵ and Ar are as defined in formula (I). Suitable agents include phosphorous oxychloride (POCl₃).

The compound of formula (II) may itself be prepared by reaction of the corresponding compound of formula (III) with the corresponding compound of formula (IV).

Ar—NH—NH₂  (III)

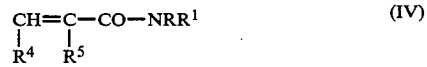

where Ar, R, R¹, R⁴ and R⁵ are as defined in formula (II).

A preferred reaction is where either R is other than hydrogen or, when R is hydrogen, R is sterically hindered by R¹ which is therefore a group such as tert-butyl.

(2) Another method, wherein, in formula (I), R¹ does not include phenyl, comprises reaction of a compound of formula (VI) with a compound of formula (V):

R¹—X  (V)

-continued

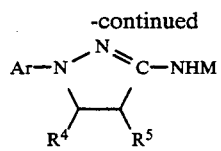

(VI)

wherein Ar, $R^4$, $R^5$ and $R^1$ are as defined in formula (I); X is a standard leaving group e.g. halo e.g. chloro or bromo; and M is an alkali or alkaline earth metal.

The reaction is preferably carried out at from 0° to 30°, more preferably at from 0° to 10° C.

The compound of formula (VI) is prepared by metallating the corresponding compound of formula (VIA):

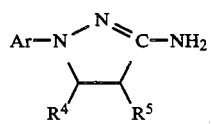

(VIA)

wherein Ar, $R^4$ and $R^5$ are as defined in formula (VI). Suitable metallating agents include an alkyl alkali metal such as a butyl metal and the reaction is preferably carried out at from $-70°$ C. to room temperature, more preferably at about $-40°$ C. The compound of formula (VI) need not be isolated but may be converted to the compound of formula (I) in situ.

(3) A further method, wherein, in formula (I), R is H and $R^1$ is other than a group having a terminal acetylenic hydrogen atom, comprises reaction of a compound of formula (VII) with $R^8Y$

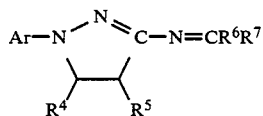

(VII)

wherein Ar, $R^4$ and $R^5$ are as defined in formula (I); Y is an alkali metal or an alkaline earth metal halide; and —$CR^6R^7R^8$ is $R^1$ as defined in formula (I). For example, $R^8Y$ is an alkyl alkaline earth metal halide such as a Grignard agent for example methylmagnesium iodide; or an alkyl alkali metal such as butyl lithium. For example, a method of preparing a compound of formula (I) wherein $R^1$ is isopropyl comprises reaction of a compound of formula (VII) wherein $R^6$ is H and $R^7$ is methyl with methyl magnesium iodide. Preferably, Ar does not include a carboxy group.

(4) A further method wherein R is hydrogen comprises reduction of a compound of formula (VII) wherein Ar, $R^4$ and $R^5$ are as defined in formula (I); and —$CHR^6R^7$ is $R^1$ as defined in formula (I).

Suitable reducing agents are known to those skilled in the art and include sodium borohydride or another metallic reducing agent such as sodium cyano-borohydride; or, where $R^1$ does not include a $>C=C<$ or a —$C\equiv C$—, by catalytic reduction using, for example, a catalyst such as platinum or palladium on carbon.

(5) A further method, wherein, in formula (I), R is hydrogen and $R^1$ includes a methylene adjacent the nitrogen atom and preferably does not include alkynyl, comprises reduction of a compound of formula (X):

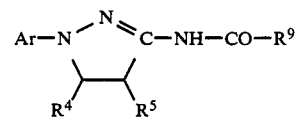

(X)

wherein Ar, $R^4$ and $R^5$ are as defined in formula (I) and $CH_2R^9$ is $R^1$ as defined in formula (I). For example, if $R^1$ is methyl, $R^9$ is hydrogen; or if $R^1$ is ethyl, $R^9$ is methyl. Suitable reducing agents are known to those skilled in the art and include diborane and lithium aluminium hydride.

The compounds of formula (I) may be used in the relief of rheumatoid arthritis, rheumatoid spondylitis, osteroarthritis, gouty arthritis and other arthritic conditions; inflamed joints; eczema, other inflammatory skin conditions; inflammatory eye conditions including conjunctivitis; pyresis and other conditions associated with inflammation and pain.

The compounds of formula (I) may also be used in the treatment or prophylaxis of allergic conditions and other airway inflammatory conditions such as asthma and of asthma having a non-allergic origin and bronchitis.

The amount required of a compound of formula (I) (hereinafter referred to as the active ingredient) for therapeutic effect will, of course, vary both with the particular compound, the route of administration and the mammal under treatment. A suitable dose of a compound of formula (I) for a mammal suffering from an inflammatory, painful or pyretic condition as defined hereinbefore is 0.5 to 500 mg of base per kilogram bodyweight, the most preferred dosage being 0.5 to 50 mg/kg of mammal bodyweight, for example 5 to 25 mg/kg; administered two or three times daily.

In the case of the treatment or prophylaxis of inflammatory airway conditions, a suitable anti-asthmatic dose of a compound of formula (I) is 1 mg to 10 mg of base per kilogram bodyweight, the most preferred dosage being 1 mg to 5 mg/kg of mammal bodyweight, for example from 1 to 2 mg/kg.

While it is possible for an active ingredient to be administered alone as the raw chemical, it is preferable to present it as a pharmaceutical formulation. Conveniently, the active ingredient comprises from 0.1% to 99.9% by weight of the formulation. Conveniently, unit doses of a formulation contain between 0.1 mg and 1 g of the active ingredient. For topical administration, the active ingredient preferably comprises from 1% to 2% by weight of the formulation but the active ingredient may comprise as much as 10% w/w. Formulations suitable for nasal or buccal administration, (such as self-propelling or powder-dispensing formulations described hereinafter), may comprise 0.1 to 20% w/w, for example about 2% w/w of active ingredient.

The formulations, both for veterinary and for human medical use, of the present invention comprise a non-toxic, effective arachidonic acid oxygenation inhibitory amount of an active ingredient together with one or more pharmaceutically acceptable carrier(s) therefor and optionally other therapeutic ingredient(s). The carrier(s) must be 'acceptable' in the sense of being compatible with the other ingredients of the formulation and not deleterious to the recipient thereof.

The formulations include those suitable for oral, rectal, parenteral (including subcutaneous, intramuscular and intravenous) topical, or nasal administration.

The formulations may conveniently be presented in unit dosage form and may be prepared by any of the methods well known in the art of pharmacy. All methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

Formulations of the present invention suitable for oral administration may be presented as discrete units such as capsules, cachets, tablets, or lozenges each containing a predetermined amount of the active ingredient; as a powder or granules; or as a solution or a suspension of an aqueous liquid or non-aqueous liquid; or as an oil-in-water emulsion or a water-in-oil emulsion. The active ingredient may also be presented as a bolus, electuary or paste.

A tablet may be made by compression or moulding, optionally with one or more accessory ingredients. Compressed tablets may be prepared by compressing, in a suitable machine, the active ingredient in a free-flowing form such as a powder or granules, optionally mixed with a binder, lubricant, inert diluent, surface active or dispersing agent. Moulded tablets may be made by moulding, in a suitable machine, a mixture of the powdered active ingredient and suitable carriers moistened with an inert liquid diluent.

Formulations for rectal administration may be presented as a suppository with the usual carriers such as cocoa butter.

Formulations suitable for parenteral administration conveniently comprise sterile aqueous preparations of the active ingredient which are preferably isotonic with the blood of the recipient.

Formulations suitable for topical administration include liquid or semi-liquid preparations such as liniments, lotions, applications; oil-in-water or water-in-oil emulsions such as creams, ointments or pastes; or solutions or suspensions such as drops.

Formulations suitable for administration to the nose or buccal cavity include powder, self-propelling and spray formulations such as aerosols and and atomizers. The formulations, when dispersed, preferably have a particle size of 10 to 200μ.

Such formulations are most preferably in the form of finely comminuted powders for pulmonary administration from a powder inhalation device or self-propelling powder-dispensing formulations, where the active ingredient finely comminuted powder may comprise up to 99.9% w/w of the formulation. In the case of self-propelling solution and spray formulations this effect may be achieved by choice of a valve having desired spray characteristic i.e. being capable of producing a spray having the desired particle size or by incorporating the medicament as a suspended powder of controlled particle size. Thus the formulation, instead of passing into the lungs, is largely retained in the nasal cavity. These self-propelling formulations may be either powder-dispensing formulations or formulations dispensing the active ingredient in the form of droplets of a solution or suspension.

Self-propelling powder-dispensing formulations preferably comprise dispersed particles of solid active ingredient, and a liquid propellant having a boiling point of below 65° F. (18° C.) at atmospheric pressure. The liquid propellant may be any propellant known to be suitable for medicinal administration and may comprise one or more lower alkyl hydrocarbons, or halogenated lower alkyl hydrocarbons, or mixtures thereof. Chlorinated and fluorinated lower alkyl hydrocarbons are especially preferred as propellant. Generally the propellant may constitute 50 to 99.9% w/w of the composition whilst the active ingredient may constitute 0.1 to 20% w/w, for example, about 2% w/w, of the formulation.

The pharmaceutically acceptable carrier in such self-propelling formulations may include other constituents in addition to the propellant, in particular a surfactant or a solid diluent or both. Surfactants are desirable in preventing agglomeration of the particles of active ingredients and in maintaining the active ingredient in suspension. Especially valuable are liquid non-ionic surfactants and solid anionic surfactants or mixtures thereof. Suitable liquid non-ionic surfactants are those having a hydrophile-lipophile balance (HLB, see Journal of the Society of Cosmetic Chemists Vol 1 pp 311–326 (1949) of below 10, in particular esters and partial esters of fatty acids with aliphatic polyhydric alcohols, for instance, sorbitan monooleate and sorbitan trioleate, known commercially as 'Span 80' (Trade Name) and 'Span 85' (Trade Name), respectively. The liquid non-ionic surfactant may constitute from 0.01 up to 20% w/w of the formulation, though preferably it constitutes below 1% w/w of the formulation. Suitable solid anionic surfactants include alkali metal, ammonium and amine salts of dialkyl sulphosuccinate, where the alkyl groups have 4 to 12 carbon atoms, and alkylbenzene sulphonic acid where the alkyl group has 8 to 14 carbon atoms. The solid anionic surfactants may constitute from 0.01 up to 20% w/w of the formulation though preferably below 1% w/w of the formulation.

Solid diluents may be advantageously incorporated in such self-propelling compositions where the density of the active ingredient differs substantially from the density of the propellant; also in order to help maintain the active ingredient in suspension. The solid diluent is in the form of a fine powder, preferably having a particle size of the same order as that of the particles of the active ingredient. Suitable solid diluents include sodium chloride, sodium sulphate and a sugar.

Formulations of the present invention may also be in the form of a self-propelling formulation wherein the active ingredient is present in solution. Such self-propelling formulations may comprise an active ingredient, propellant and co-solvent, and advantageously an antioxidant stabiliser. The propellant is one or more of those already cited above. Co-solvents are chosen for their solubility in the propellant, their ability to dissolve the active ingredient, and for their having the lowest boiling point consistent with these above-mentioned properties. Suitable co-solvents are lower alkyl alcohols and ethers and mixtures thereof. The co-solvents may constitute 5 to 40% w/w of the formulation, though preferably less than 20% w/w of the formulation.

Antioxidant stabilisers may be incorporated in such solution-formulations to inhibit deterioration of the active ingredient and are conveniently alkali metal ascorbates or bisulfites. They are preferably present in an amount of up to 0.25% w/w of the formulation.

Such self-propelling formulations may be prepared by any method known in the art. For example the active ingredient either as particles as defined hereinbefore in suspension in a suitable liquid or in up to 20% w/v solution in an acceptable co-solvent as appropriate, is mixed with any other constituents of a pharmaceutically acceptable carrier. The resulting mixture is cooled and introduced into a suitable cooled container and propellant is added thereto in liquid form; and the container is sealed.

Alternatively such self-propelling formulations may be prepared by mixing the active ingredient either in particles as hereinbefore defined or in 2 to 20% w/v alcohol or aqueous solution as appropriate, together with the remaining constituents of the pharmaceutically acceptable carrier other than propellant; introducing the resulting mixture, optionally with some propellant, into a suitable container; and injecting propellant under pressure into the container at ambient temperature through a valve which comprises a part of the container and is used to control release of the formulation from it. Desirably the container is purged by removing air from it at a convenient stage in the preparation of the self-propelling formulation.

A suitable container for a self-propelling formulation is one provided with a manually operable valve and being constructed of aluminium, stainless steel or reinforced glass. The valve should of course be one having the desired spray characteristics of particle size as hereinbefore defined. Advantageously the valve of the type which delivers a fixed amount of formulation on the occasion of each operation of the valve, for example, about 50 or 100 microliters of formulation in each delivery.

Formulations of the present invention may also be in the form of aqueous or dilute alcoholic solution, optionally a sterile solution, of the active ingredient for use in a nebuliser or atomiser, wherein an accelerated air stream is used to produce a fine mist consisting of small droplets of the solution. Such formulations usually contain a flavouring agent such as saccharin sodium and a volatile oil. A buffering agent such as sodium metabisulfite and a surface active agent may also be included and such a formulation should contain a preservative such as methylhydroxybenzoate.

Other formulations suitable for nasal administration include a coarse powder having a particle size of 20 to 500 microns which is administered in the manner in which snuff is taken i.e. by rapid inhalation through the nasal passage from a container of the powder held close up to the nose.

In addition to the aforementioned ingredients, the formulations of this invention may include one or more additional ingredients such as diluents, buffers, flavouring agents, binders, surface active agents, thickeners, lubricants, preservatives e.g. methylhydroxybenzoate (including anti-oxidants), emulsifying agents and the like.

According to the present invention there are therefore provided:

(a) a novel compound of formula (I) or an acid addition salt thereof;
(b) a method for preparing a compound of formula (I);
(c) a pharmaceutical formulation comprising a non-toxic, effective arachidonic acid oxygenation inhibitory amount of a compound of formula (I) or a pharmaceutically acceptable salt thereof and a pharmaceutically acceptable carrier therefor;
(d) a method for preparing such formulations;
(e) a method for the prophylaxis or treatment of inflammation in a mammal, including man, comprising the administration to said mammal of a non-toxic, effective anti-inflammatory amount of a compound of formula (I);
(f) a method for the prophylaxis or treatment of pain in a mammal, including man, comprising the administration to said mammal of a non-toxic, effective analgesic amount of a compound of formula (I);
(g) a method for the prophylaxis or treatment of pyresis in a mammal, including man, comprising the administration to said mammal of a non-toxic, effective anti-pyretic amount of a compound of formula (I);
(h) a method for the prophylaxis or treatment of asthma in a mammal, including man, comprising the administration to said mammal of a non-toxic, effective, anti-asthmatic amount of a compound of formula (I);
(i) a method for the inhibition of a pathway of arachidonic acid oxygenation selected from the lipoxygenase and cyclo-oxygenase pathways, comprising the administration of a non-toxic, effective, inhibitory amount of a compound of formula (I) or a pharmaceutically acceptable acid addition salt thereof; and
(j) a compound of formula (I) for use in medicine in the inhibition of the lipoxygenase or cyclo-oxygenase pathways of arachidonic acid metabolism.

The following Examples are provided by way of an illustration of the present invention and should in no way be construed as a limitation thereof. All temperatures indicated are in degrees Celsius.

EXAMPLE 1

Preparation of 3-methylamino-1-(3-trifluoromethylphenyl)-2-pyrazoline

3-Formamido-1-(3-trifluoromethylphenyl)-2-pyrazoline (2.4 g) was stirred with dry diethyl ether (60 ml) to produce a slurry which was gradually added to a stirred ice-cold suspension of lithium aluminium hydride (1.0 g) in dry diethyl ether (75 ml) under a nitrogen atmosphere. The addition took place over a period of about 20 minutes and was accompanied by a vigorous reaction. The final reaction mixture was stirred for a further 15 minutes and was then carefully and slowly decomposed by the addition of water (30 ml). The ethereal layer was then decanted off the aqueous sludge which was washed twice with diethyl ether. The combined ethereal solutions were dried over potassium carbonate, filtered and evaporated. The resulting 3-methylamino-1-(3-trifluoromethylphenyl)-2-pyrazoline was a colourless crystalline solid on precipitation by benzene and recrystallization with light petroleum, yield 1.8 g, m.p. 93.1°. The hydrochloride was recrystallized by precipitation from methanol with ether and light petroleum m.p. 206°–207°.

EXAMPLE 2

Preparation of 3-ethylamino-1-(3-trifluoromethylphenyl)-2-pyrazoline

By a method analogous to that described in Example 1 3-acetamido-1-(3-trifluoromethylphenyl)-2-pyrazoline was reduced with lithium aluminium hydride, using tetrahydrofuran in place of diethyl ether. The hydrochloride of the resulting 3-ethylamino-1-(3-trifluoromethylphenyl)-2-pyrazoline was recrystallized from isopropanol and diethylether, m.p. 171.5°.

EXAMPLE 3

Preparation of 3-propylamino-1-(3-trifluoromethylphenyl)-2-pyrazoline

3-Propionamido-1-(3-trifluoromethylphenyl)-2-pyrazoline was prepared from propionic anhydride and 3-amino-1-(3-trifluoromethylphenyl)-2-pyrazoline in refluxing chloroform and crystallized from methanol m.p. 175.2°. It was then reduced with lithium aluminium hydride in diethyl ether according to the method described in Example 1 to give 5-propylamino-1-(3-trifluoromethylphenyl)-2-pyrazoline which was recrystallized as the hydrochloride m.p. 151.2°.

EXAMPLE 4

Preparation of 3-butylamino-1-(3-trifluoromethylphenyl)-2-pyrazoline

According to the method of Example 1, 3-butyramido-1-(3-trifluoromethylphenyl)-2-pyrazoline was reduced with lithium aluminium hydride to produce 3-butylamino-1-(3-trifluoromethylphenyl)-2-pyrazoline which was a gum (yield 2.4 g) and was recrystallized as the hydrochloride m.p. 173.4° (yield 1.65 g).

EXAMPLE 5

Preparation of 3-benzylamino-1-(3-trifluoromethylphenyl)-2-pyrazolinehydrochloride 3-Amino-1-(3-trifluoromethylphenyl)-2-pyrazoline (460 mg) and benzaldehyde (220 mg) were dissolved together in ethanol (2 ml) and the solution was heated to reflux for 2 hours. On cooling, the separated 3-benzylideneamino-1-(3-trifluoromethylphenyl)-2-pyrazoline was collected and recrystallized from ethanol, m.p. 159°-160°.

3-Benzylideneamino-1-(3-trifluoromethylphenyl)-2-pyrazoline (1.6 g) was then suspended in ethanol (10 ml) at room temperature under a nitrogen atmosphere. The mixture was stirred and sodium borohydride (2.0 g) was added. After stirring for some 2 hours, a clear light-yellow solution formed, which was poured onto ice and diethyl ether. The aqueous portion was removed, the residual diethyl ether was washed with fresh water and then with 2N-hydrochloric acid. A crystalline solid separated which was collected, washed with fresh diethyl ether and then with fresh 2N-hydrochloric acid. The resulting 3-benzylamino-1-(3-trifluoromethylphenyl)-2-pyrazoline hydrochloride was recrystallized from methanol, diethyl ether and light petroleum, m.p. 190.3° (yield 890 mg).

EXAMPLE 1A

Preparation of starting material of Example 1

3-Amino-1-(3-trifluoromethylphenyl)-2-pyrazoline (1.907 g) was dissolved in formic acid (20 ml). The solution was stirred at 60° and acetic anhydride (2.4 ml) was added dropwise. The mixture was heated for 1 hour at 60° and then poured into water and stirred to decompose the residual excess anhydride. 3-Formamido-1-(3-trifluoromethylphenyl)-2-pyrazoline resulted as a crystalline solid m.p. 128°-129°. This compound was then used to prepare the compound of Example 1, as hereinbefore described.

EXAMPLE 6

Preparation of 3-ethylamino-5-methyl-1-phenyl-2-pyrazoline 3-Acetamido-5-methyl-1-phenyl-2-pyrazoline 3-Amino-5-methyl-1-phenyl-2-pyrazoline (Duffin & Kendall, J. Chem. Soc., 1954, 408) (4.37 g) was added, with stirring, to acetic anhydride (4 ml). After 10 minutes water was added and the precipitated solid was extracted into chloroform. The extract was washed with water, dried and evaporated to give the acetamido-compound, which crystallised from methanol in small colourless needles, m.p. 134°-136°.

Analysis: $C_{12}H_{15}N_3O$ Required: C, 66.3; H, 7.0; N, 19.3, Found: C, 66.4, H, 7.2; N, 19.7.

3-Ethylamino-5-methyl-1-phenyl-2-pyrazoline

The acetamido-compound (3.07 g) was added to a stirred suspension of lithium aluminium hydride (1.56 g) in dry ether (70 ml). The mixture was refluxed for 5 hours, then left at room temperature for 16 hours. Water (1.5 ml), 2N-sodium hydroxide solution (1.5 ml) and water (4.5 ml) were added successively and the resulting solid was removed by filtration. The ether filtrate was extracted with N-hydrochloric acid ($2 \times 10$ ml), the acidic solution was basified with dilute sodium hydroxide solution and the precipitated oil was extracted into ether. The washed and dried ether solution was evaporated and the residue was distilled to give 3-ethylamino-5-methyl-1-phenyl-2-pyrazoline, b.p. 125°-127°/0.05 mm.

Analysis: $C_{12}H_{17}N_3$, Required: C, 70.9; H, 8.4; N, 20.7, Found: C, 71.1; H, 8.7; N, 20.6.

EXAMPLE 7

Preparation of 3-butylamino-5-methyl-1-phenyl-2-pyrazoline 3-Butyramido-5-methyl-1-phenyl-2-pyrazoline 3-Amino-5-methyl-1-phenyl-2-pyrazoline (8.75 g) was added, with stirring, to butyric anhydride (16 ml) and the mixture was stirred at room temperature for 45 minutes. Water was added and the precipitated oil was extracted with chloroform. The extract was washed with water, dried and evaporated. The residue was dissolved in toluene and purified by chromatography on a column of neutral alumina to give the butyramido-compound, m.p. 73°-75° after recrystallisation from cyclohexane.

Analysis: $C_{14}H_{19}N_3O$, Required: C, 68.5; H, 7.8; N, 17.1, Found: C, 68.7; H, 8.2; N, 17.3.

3-Butylamino-5-methyl-1-phenyl-2-pyrazoline

The butyramido-compound was reduced with lithium aluminium hydride as described in Example 6 to give the butylamino-compound, b.p. 143°-144°/0.05 mm.

Analysis: $C_{14}H_{21}N_3$, Required: C, 72.7; H, 9.2; N, 18.2, Found: C, 73.0; H, 9.3; N, 18.4.

EXAMPLE 8

3-Amine-1-(4-chlorophenyl)-2-pyrazoline (1.8 g) was dissolved in anhydrous formic acid (10 ml) at room temperature in an atmosphere of nitrogen. Acetic anhydride (2.66 ml) was added dropwise over a period of 5 minutes and the resulting mixture, still under nitrogen, was heated to 60° for 15 minutes. Water was then added at about 20° until a crystalline sold separated. The resulting 3-formamido-1-(4-chlorophenyl)-2-pyrazoline was collated and recrystallised from methanol, m.p. 154°–155° (yield 1.425 g).

Analysis: $C_{10}H_{10}ClN_3O$, Required: C, 53.70; H, 4.51; N, 18.79, Found: C, 53.89; H, 4.51; N, 18.48.

A solution of the formamido compound (1.425 g) in dry tetrahydrofuran (15 ml) was added to a stirred suspension of lithium aluminium hydride (1.74 g) in dry tetrahydrofuran (1.74 g) in an atmosphere of nitrogen at 0°. The resulting mixture was stirred at room temperature for 2 hours and was then cautiously decomposed with water in the usual way, still under nitrogen. The organic layer was separated and the residual aqueous sludge extracted twice with ether. The combined organic layers were dried over potassium carbonate, and evaporated. The residue was reacted with a slight excess of concentrated hydrochloric acid in methanol, when evaporation gave 3-methylamino-1-(4-chlorophenyl)-2-pyrazoline hydrochloride. It was recrystallised from isopropanol, m.p. 168°–169° (yield 1.187 g).

Analysis: $C_{10}H_{12}ClN_3 \cdot HCl$, Required: C, 48.8; H, 5.32; N, 17.07, Found: C, 48.15; H, 5.41; N, 17.10.

EXAMPLE 9

3-Amino-1-(2-pyridyl)-2-pyrazoline (1.5 g) was added to formic acid (22 ml) at 60° in an atmosphere of nitrogen. The mixture was stirred whilst acetic anhydride (2.3 ml) was added dropwise. The mixture was heated at 100° for 1 hour before being evaporated in vacuo to give 3-formamido-1-(2-pyridyl)-2-pyrazoline which was recrystallised from isopropanol, m.p. 182°–183° (yield 1.17 g).

A solution of the formamido compound (1.15 g) in dry tetrahydrofuran (100 ml) was added dropwise to a stirred suspension of lithium aluminium hydride (1.65 g) in dry tetrahydrofuran (16.5 ml) in an atmosphere of nitrogen. After stirring for 1 hour at room temperature, the final mixture was heated to reflux for 2 hours before being decomposed with water in the usual way. The organic layer was then separated, the residue washed twice with fresh ether and the combined organic layers dried over potassium carbonate before filtration and evaporation. The resulting crude base was taken up into methaonol and a slight excess of 2N-hydrochloric acid (3.1 ml) was added. Evaporation gave a rather sticky product which solidified on trituration with isopropanol. The resulting 3-methylamino-1-(2-pyridyl)-2-pyrazoline hydrochloride was a yellow solid, m.p. 263° (yield 200 mg).

Analysis: $C_9H_{13}ClN_4$, Required: C, 50.82; H, 6.16; N, 26.34; Cl, 16.67, Found: C, 50.36; H, 6.29; N, 25.87; Cl, 16.25.

EXAMPLE 10

Isobutyric anhydride (5 ml) was added to a solution of 3-amino-1-(3-trifluoromethylphenyl)-2-pyrazoline (5 g) in chloroform (30 ml) and the mixture heated to reflux for 1 hour. The excess anhydride was decomposed by the addition of ethanol (5 ml) and refluxed for a further 30 minutes. The cooled mixture was extracted with 2N-sodium hydroxide, dried over potassium carbonate and evaporated to give a dark brown gum which crystallised over a period of days. Trituration with ether gave a dark coloured solid m.p. 164° (2.265 g) which was recrystallised from light petroleum (b.p. 80°–100°) to give 3-isobutyramido-1-(3-trifluoromethylphenyl)-2-pyrazoline (1.77 g) m.p. 167°–168°.

A solution of the isobutyramido compound (1.72 g) in dry tetrahydrofuran (15 ml) was added dropwise to a suspension of lithium aluminium hydride (1.5 g) in dry tetrahydrofuran (15 ml) at 0° and in an atmosphere of nitrogen. After stirring at room temperature for 2 hours, the mixture was heated to reflux for 2 hours. It was finally cooled and decomposed with water in the usual way. The organic layer was separated, the residual sludge washed twice with ether and all the combined extracts dired over potassium carbonate, then filtered and evaporated. The residue was reacted with a slight excess of 2N-hydrochloric acid to give 3-(3-methylpropylamino)-1-(3-trifluoromethylphenyl)-2-pyrazoline hydrochloride, m.p. 143°–144° (1.0 g).

Analysis: $C_{14}H_{18}F_3N_3$, Required: C, 50.26; H, 5.95; N, 13.06, Found: C, 52.53; H, 6.04; N, 13.00.

EXAMPLE A

Tablet

|  | In one tablet |
| --- | --- |
| Active Ingredient | 5.0 mg |
| Lactose | 82.0 mg |
| Starch | 10.0 mg |
| Povidone | 2.0 mg |
| Magnesium Stearate | 1.0 mg |

Mix together the active ingredient, lactose and starch. Granulate the powders using a solution of povidone in purified water. Dry the granules, add the magnesium stearate and compress to produce tablets, 100 mg per tablet.

EXAMPLE B

Ointment

| Active Ingredient | 1.0 g |
| --- | --- |
| White Soft Paraffin to | 100.0 g |

Disperse the active ingredient in a small volume of the vehicle. Gradually incorporate this into the bulk to produce a smooth, homogeneous product. Fill into collapsible metal tubes.

EXAMPLE C

Cream for Topical Use

| Active Ingredient | 1.0 g |
| --- | --- |
| Polawax GP 200 | 20.0 g |
| Lanolin Anhydrous | 2.0 g |

| White Beeswax | 2.5 g |
| --- | --- |
| Methyl Hydroxybenzoate | 0.1 g |
| Distilled Water to | 100.0 g |

Heat the Polawax, beeswax and lanolin together at 60° C. Add a solution of methyl hydroxybenzoate. Homogenise using high speed stirring. Allow the temperature to fall to 50°. Add and disperse the active ingredient. Allow to cool with slow speed stirring.

EXAMPLE D

Lotion for Topical Use

| | |
|---|---|
| Active Ingredient | 1.0 g |
| Sorbitan Monolaurate | 0.6 g |
| Polysorbate 20 | 0.6 g |
| Cetostearyl Alcohol | 1.2 g |
| Glycerin | 6.0 g |
| Methyl Hydroxybenzoate | 0.2 g |
| Purified Water B.P. to | 100.0 ml |

The methyl hydroxybenzoate and glycerin were dissolved in 70 ml of the water at 75° C. The sorbitan monolaurate, Polysorbate 20 and cetostearyl alcohol were melted together at 75° C. and added to the aqueous solution. The resulting emulsion was homogenised, allowed to cool with continuous stirring and the active ingredient added as a suspension in the remaining water. The whole was stirred until homogeneous.

EXAMPLE E

Eye Drops

| | |
|---|---|
| Active Ingredient | 0.5 g |
| Methyl Hydroxybenzoate | 0.01 g |
| Propyl Hydroxybenzoate | 0.04 g |
| Purified Water B.P. | 100.00 ml |

The methyl and propyl hydroxybenzoates were dissolved in 70 ml purified water at 75° and the resulting solution then allowed to cool. The active ingredient was added next and the solution made up to 100 ml with purified water. The solution was sterilised by filtration through a membrane filter 0.22 μm pore size and packed aseptically into suitable sterile containers.

EXAMPLE F

Injection Solution

| | |
|---|---|
| Active Ingredient | 10.0 mg |
| Water for Injections B.P. to | 1.0 ml |

The active ingredient was dissolved in half of the Water for Injections and then made up to volume and sterilised by filtration. The resulting solution was distributed into ampoules under aseptic conditions.

EXAMPLE I

Inhibition of Lipoxygenase and Cyclo-oxygenase

In an enzyme assay according to the method of G Blackwell and R J Flower (Br. J. Pharmac., 63: 360P (1978)), compounds of the invention were found to have an $ED_{50}$ (μM) for inhibition of each of lipoxygenase and cyclo-oxygenase as indicated in Table I:

TABLE I

| | $ED_{50}$ (μM) | |
|---|---|---|
| Compound | Cyclo-oxygenase | lipoxygenase |
| of Example 1 | ~0.3 | ~0.3 |
| of Example 2 | ~0.8 | ~0.7 |
| of Example 3 | <0.3 | <0.3 |

TABLE I-continued

| | $ED_{50}$ (μM) | |
|---|---|---|
| Compound | Cyclo-oxygenase | lipoxygenase |
| of Example 4 | <0.3 | <0.3 |
| of Example 5 | ~0.3 | ~0.3 |

We claim:
1. A compound selected from the group consisting of:
3-(methylamino)-1-(3-trifluoromethylphenyl)-2-pyrazoline;
3-(ethylamino)-1-(3-trifluoromethylphenyl)-2-pyrazoline;
3-(n-propylamino)-1-(3-trifluoromethylphenyl)-2-pyrazoline;
3-(iso-propylamino)-1-(3-trifluoromethylphenyl)-2-pyrazoline;
3-(n-butylamino)-1-(3-trifluoromethylphenyl)-2-pyrazoline;
3-(sec-butylamino)-1-(3-trifluoromethylphenyl)-2-pyrazoline;
3-(tert-butylamino)-1-(3-trifluoromethylphenyl)-2-pyrazoline;
3-(methylpropylamino)-1-(3-trifluoromethylphenyl)-2-pyrazoline;
3-(benzylamino)-1-(3-trifluoromethylphenyl)-2-pyrazoline;
3-(N,N-dimethylamino)-1-(4-trifluoromethylphenyl)-2-pyrazoline;
3-(methylamino)-1-(4-chlorophenyl)-2-pyrazoline;
3-(N-methyl-N-ethylamino)-1-(4-chlorophenyl)-2-pyrazoline;
3-(methylamino)-1-(4-fluorophenyl)-5-methyl-2-pyrazoline;
3-(benzylamino)-1-(4-bromophenyl)-4-methyl-2-pyrazoline;
3-(ethylamino)-1-(3-trifluoromethyl-4-fluorophenyl)-2-pyrazoline;
3-(tert-butylamino)-1-(3-trifluoromethyl-4-bromophenyl)-2-pyrazoline;
3-(allylamino)-1-(3-trifluoromethylphenyl)-2-pyrazoline;
3-(cyclohexylmethylamino)-1-(3-trifluoromethylphenyl)-2-pyrazoline; or an
acid addition salt thereof.
2. A compound selected from the group consisting of:
3-methylamino-1-(3-trifluoromethylphenyl)-2-pyrazoline;
3-ethylamino-1-(3-trifluoromethylphenyl)-2-pyrazoline;
3-propylamino-1-(3-trifluoromethylphenyl)-2-pyrazolinehydrochloride;
3-butylamino-1-(3-trifluoromethylphenyl)-2-pyrazoline hydrochloride;
3-benzylamino-1-(3-trifluoromethylphenyl)-2-pyrazolinehydrochloride;
3-methylamino-1-(4-chlorophenyl)-2-pyrazoline hydrochloride; and
3-(3-methylpropylamino)-1-(3-trifluoromethylphenyl)-2-pyrazoline hydrochloride.
3. A compound selected from 3-(methylamino)-1-(3-trifluoromethylphenyl)-2-pyrazoline or an acid addition salt thereof.
4. 3-(methylamino)-1-(3-trifluoromethylphenyl)-2-pyrazoline.
5. A pharmaceutically acceptable acid addition salt of the compound of claim 4.

* * * * *